United States Patent [19]

Petusky

[11] Plant 4,482

[45] Nov. 13, 1979

[54] CHRYSANTHEMUM NAMED GOLDEN BOUNTY

[75] Inventor: Kerry S. Petusky, West Chicago, Ill.

[73] Assignee: Pan-American Plant Company, West Chicago, Ill.

[21] Appl. No.: 963,883

[22] Filed: Nov. 27, 1978

[51] Int. Cl.[2] ..... A01H 5/03

[52] U.S. Cl. ..... Plt./78

[58] Field of Search ..... Plt./78

*Primary Examiner*—Robert E. Bagwill

*Attorney, Agent, or Firm*—Chas. W. Rummler

[57] ABSTRACT

A new variety of chrysanthemum of the composite and incurved standard type distinguished by the bright yellow color of its medium sized blooms, its year around flowering capability with photoperiod control, its nine-week response, and its vigorous, upright and terminal habit of growth.

6 Drawing Figures

BACKGROUND OF THE NEW PLANT

This new chrysanthemum cultivar originated as a sport of the white blossomed variety "Bounty" (Ser. No. 955,002, filed 10-6-78) growing in greenhouse at West Chicago, Ill., and was discovered by me in 1976 during the course of my breeding efforts carried on for the purpose of developing new and improved chrysanthemum varieties. This sport was reproduced by me at West Chicago, Ill., by means of vegetative cuttings for test of its character and subsequent propagation of the new plant by cuttings through successive generations has shown that its distinctive characteristics hold true from generation to generation and appear to be firmly fixed. This plant is now being grown on a commercial scale at Cortez, Fla., as well as at West Chicago, Ill.

DESCRIPTION OF THE DRAWINGS

My new variety of chrysanthemum plant is illustrated by the accompanying drawings, one sheet of which is a photographic view showing the flower form and color characteristics of the plant in full bloom, this view having been hand painted with permanent colors to show the true flower coloring, and the second sheet being a print of a machine copy of typical leaves of this new plant at several stages of its maturity.

DESCRIPTION OF THE NEW PLANT

The following is a detailed description of my new chrysanthemum variety with color designations according to The R.H.S. Colour Chart published by The Royal Horticultural Society of London, England.

THE PLANT

Origin: Sport.

Parentage: "Bounty" (Ser. No. 955,002, filed 10-6-78).

Classification

*Botanic.*—*Chrysanthemum morifolium.*

*Commercial.*—Greenhouse cut flower plant.

Form: Perennial herbaceous bush.

Height: 104 to 125 cm.

Growth: Terminal, upright and vigorous, with sturdy stems of very good strength.

Branching: Normal when grown under natural conditions.

Foliage:

*Quantity.*—Abundant, 4 to 5 leaves on about 15 cm. of stem length.

*Size of leaf.*—Length — about 8.5 to 15.4 cm. Width — about 4.4 to 9.5 cm.

*Leaf shape.*—Lobed, lanceolate and slightly serrated.

*Surface aspect.*—Canescent.

*Color.*—Upper side — 147A. Under side — 147B.

*Venation.*—Pinnately veined.

*Petioles.*—Length — about 1.6 to 3.7 cm.

THE BUD

Form: Elliptical

Diameter: About 15 to 18 mm.

Depth: About 9 to 11 mm.

Opening Rate: The bud opens slowly.

Color:

*When phyllaries first divide.*—6D.

*When florets begin to unfurl.*—12B.

Phyllaries: The outside of the receptacle bears many involucral bracts which are upstanding and spear-shaped.

*Color.*—Inside — 137A. Outside — 137B.

*Surface aspect.*—Pubescent.

Peduncle: Erect and strong, and about 2.5 to 4.0 cm. in length.

*Surface aspect.*—Pubescent.

THE FLOWER

Flowering capability: Recommended for year around flowering with photoperiod control.

*Response.*—9 weeks.

*Natural flowering season.*—October 27 to November 5.

Blooms:

*Flower type.*—Composite and incurved standard.

*Size.*—Medium. Diameter — about 11 to 14.5 cm. Depth — about 9 to 12 cm.

*Borne.*—Singly, each bloom comprising a head of many florets borne on a receptacle.

*Shape.*—When bloom first opens — cup-shaped with a high center. As bloom matures, the shape becomes globular.

Florets: Numerous in number.

*Form.*—Linear, spoon-shaped, and incurved, with obtuse apex.

| Color: | April | June |
|---|---|---|
| Outer florets: | | |
| Upper side - | 5C | 5C |
| Reverse side - | 5D | 5D |
| Inside florets: | | |
| Upper side - | 5B | 5B |
| Reverse side - | 6D | 6D |

*Firmness.*—Medium.

*Appearance.*—A very slight shine.

*Discoloration.*—Very little fade after full bloom.

*Persistence.*—The florets hang on and dry.

Peduncle: Upright and sturdy.

*Length.*—About 2.5 to 4.0 cm.

*Color.*—147B.

Fragrance: Typical chrysanthemum.

Lasting quality:

*On plant.*—3 to 4 weeks.

*As a cut flower.*—10 to 17 days.

REPRODUCTIVE ORGANS

Stamens:

*Arrangement.*—Syngenesious. Number — 5.

*Filaments.*—About 2 to 4 mm. in length.

*Color.*—Light yellow.

*Pollen.*—Color — yellow.

Pistils:

*Number.*—1 to each ray and disc floret.

*Styles.*—4 to 6 mm. in length.

*Stigma.*—Color — yellow.

Ovaries: Inferior, bicarpellate.

This new cultivar of standard chrysanthemum, when compared to its parent variety "Bounty" (Ser. No. 955,002, filed 10-6-78), is characterized in uniqueness by the medium yellow color of its blooms. Otherwise, this new plant is quite similar to its parent with respect to its growth and flowering characteristics.

I claim:

1. A new and distinct cultivar of standard chrysanthemum of the greenhouse cut flower type, substantially as herein shown and described, particularly characterized in uniqueness, when compared with its parent variety which has white blooms, by the medium yellow coloration of the blooms.

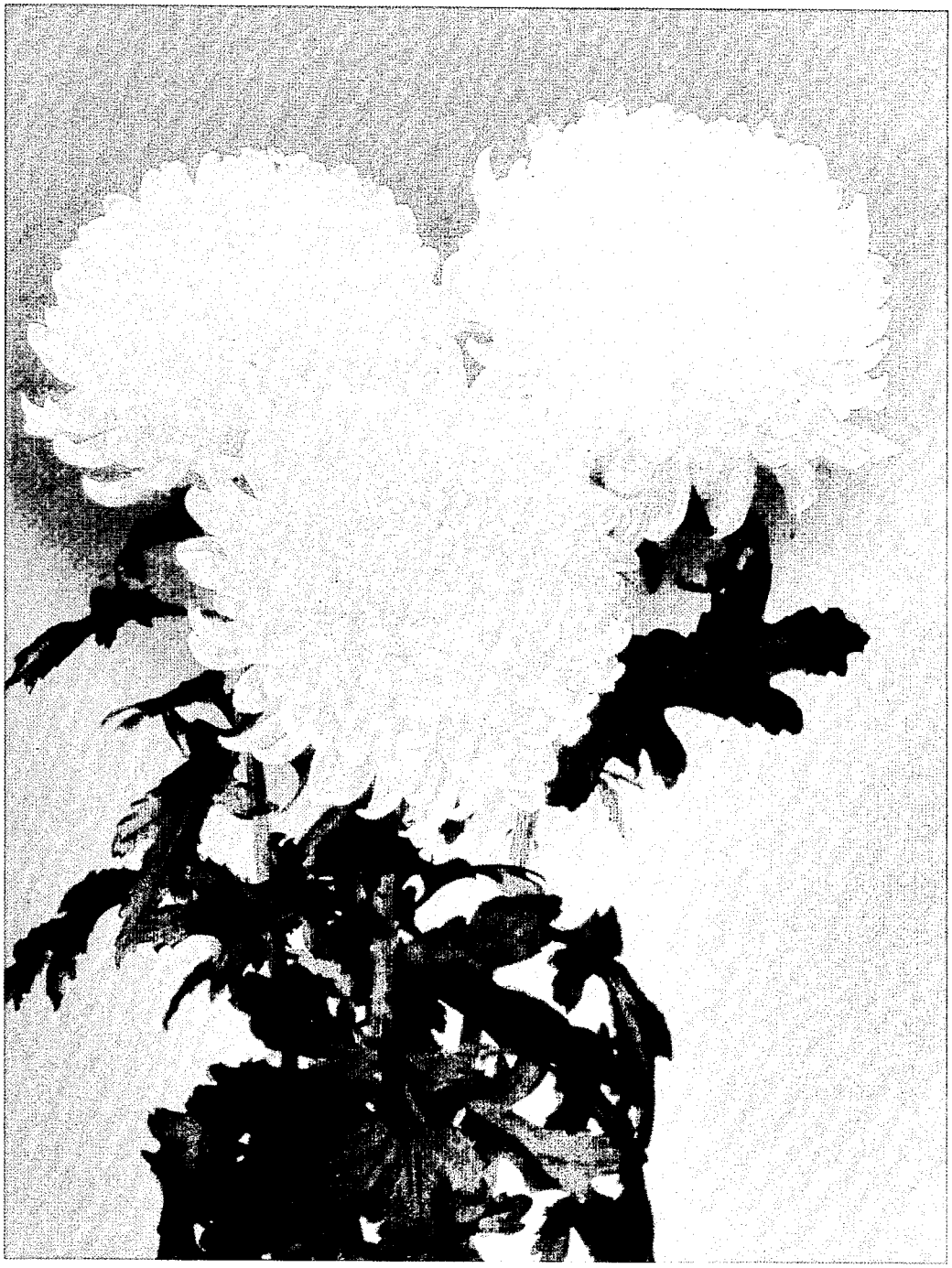

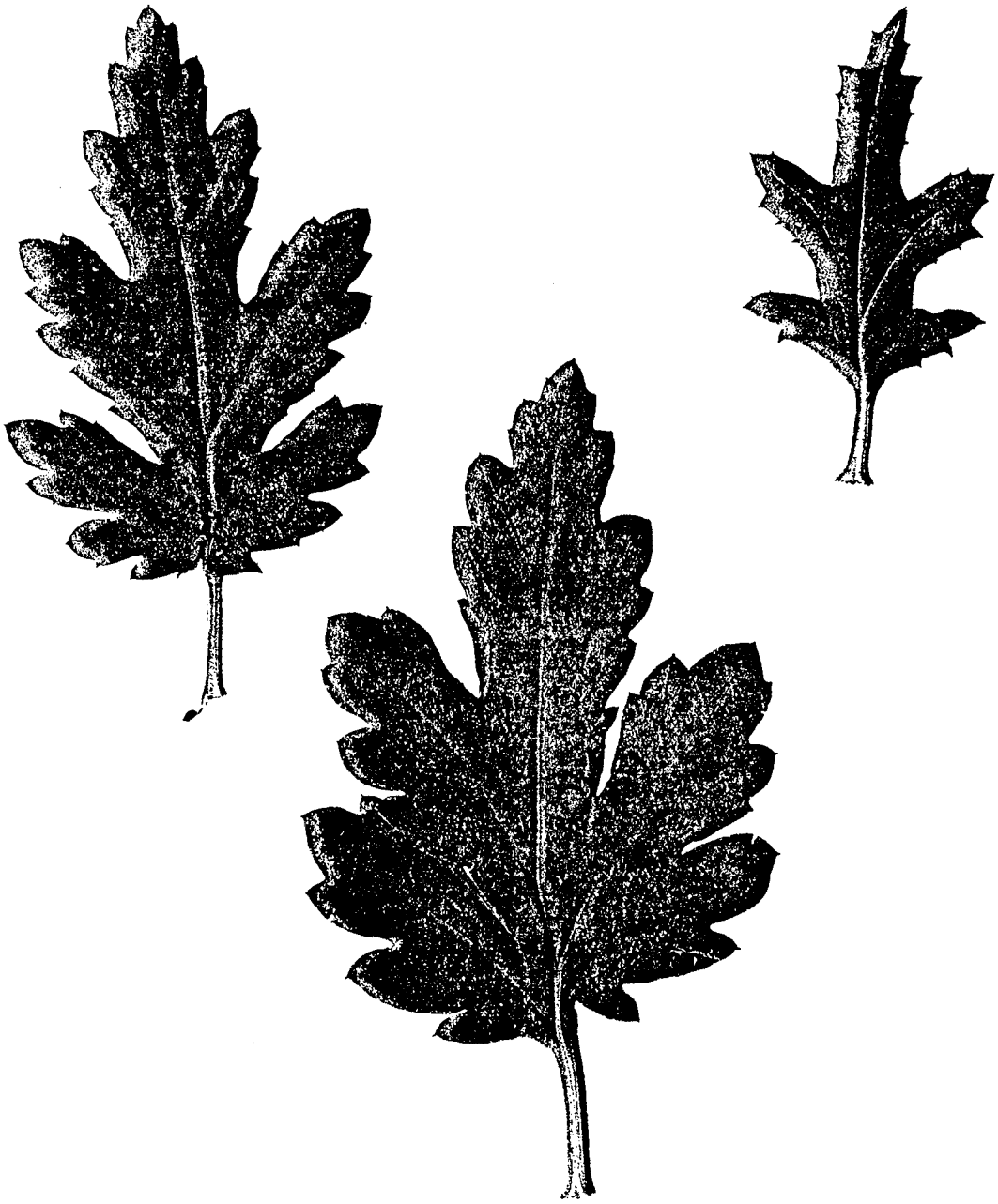

* * * * *